(12) United States Patent
Visentin

(10) Patent No.: US 8,702,708 B2
(45) Date of Patent: Apr. 22, 2014

(54) CONNECTING MEMBER INSERTABLE INSIDE A BONE STRUCTURE OF A HUMAN OR ANIMAL BODY, AND RELATED LOCATING SYSTEM

(75) Inventor: Ezio Visentin, Peseggia di Scorze (IT)

(73) Assignee: I.R.I.DE. S.R.L.—Intelligent Radioactive and Integrated Devices, Udine (IT)

( * ) Notice: Subject to any disclaimer, the term of this patent is extended or adjusted under 35 U.S.C. 154(b) by 1703 days.

(21) Appl. No.: 11/568,568

(22) PCT Filed: May 6, 2005

(86) PCT No.: PCT/IB2005/001355
§ 371 (c)(1),
(2), (4) Date: Nov. 1, 2006

(87) PCT Pub. No.: WO2005/107614
PCT Pub. Date: Nov. 17, 2005

(65) Prior Publication Data
US 2007/0282440 A1 Dec. 6, 2007

(30) Foreign Application Priority Data
May 6, 2004 (IT) .............................. TO2004A0292

(51) Int. Cl.
*A61B 17/58* (2006.01)
(52) U.S. Cl.
USPC ................................ 606/64; 606/98; 600/424
(58) Field of Classification Search
USPC .......... 600/3, 414, 424, 426, 436; 606/62, 64, 606/87, 97, 98, 104, 130; 623/16.11
See application file for complete search history.

(56) References Cited

U.S. PATENT DOCUMENTS

| | | | |
|---|---|---|---|
| 4,621,628 A * | 11/1986 | Brudermann | 606/97 |
| 4,865,025 A | 9/1989 | Buzzi et al. | |
| 5,013,317 A * | 5/1991 | Cole et al. | 606/96 |
| 5,127,913 A * | 7/1992 | Thomas, Jr. | 606/62 |
| 5,178,164 A | 1/1993 | Allen | |
| 5,322,499 A * | 6/1994 | Liprie | 600/8 |
| 5,417,688 A * | 5/1995 | Elstrom et al. | 606/64 |
| 5,540,691 A * | 7/1996 | Elstrom et al. | 606/64 |
| 5,584,838 A * | 12/1996 | Rona et al. | 606/96 |
| 5,716,358 A * | 2/1998 | Ochoa et al. | 606/62 |
| 5,873,811 A * | 2/1999 | Wang et al. | 600/3 |
| 6,074,394 A | 6/2000 | Krause | |
| 6,080,099 A | 6/2000 | Slater et al. | |

(Continued)

FOREIGN PATENT DOCUMENTS

| | | |
|---|---|---|
| DE | 10239673 | 3/2004 |
| EP | 0 187 283 | 7/1986 |

(Continued)

OTHER PUBLICATIONS

Japanese Office Action of Jan. 11, 2011 with English translation for corresponding JP patent application No. 2007-512585 (5 pages).

*Primary Examiner* — Nicholas Woodall
*Assistant Examiner* — Larry E Waggle, Jr
(74) *Attorney, Agent, or Firm* — Lucas & Mercanti, LLP

(57) ABSTRACT

A connecting member insertable, at a fracture, inside a bone structure of a human or animal body to immobilize at least two bone portions. The connecting member has at least one radioactive source located at a predetermined reference point.

22 Claims, 2 Drawing Sheets

(56) References Cited

U.S. PATENT DOCUMENTS

| | | |
|---|---|---|
| 6,175,760 B1 | 1/2001 | Baskin et al. |
| 6,273,851 B1 | 8/2001 | Slater et al. |
| 6,497,647 B1 * | 12/2002 | Tucker .................. 600/8 |
| 6,514,193 B2 * | 2/2003 | Kaplan ................. 600/7 |
| 6,616,670 B2 * | 9/2003 | Simon et al. ........... 606/62 |
| 2002/0052604 A1 | 5/2002 | Simon et al. |
| 2002/0077541 A1 * | 6/2002 | Kienzle, III ........... 600/424 |
| 2003/0036700 A1 * | 2/2003 | Weinberg ............. 600/436 |
| 2003/0139669 A1 * | 7/2003 | Montegrande ......... 600/426 |
| 2003/0192557 A1 * | 10/2003 | Krag et al. ............ 128/898 |
| 2005/0096655 A1 * | 5/2005 | Trinchese ............. 606/62 |
| 2005/0171553 A1 | 8/2005 | Schwarz et al. |

FOREIGN PATENT DOCUMENTS

| | | |
|---|---|---|
| EP | 1195143 | 4/2002 |
| JP | 61-154661 | 7/1986 |
| JP | 2002513305 | 5/2002 |
| JP | 2004-512502 | 4/2004 |
| WO | 9713467 | 4/1997 |
| WO | 02/16965 | 2/2002 |

* cited by examiner ively, the following description refers purely by
CONNECTING MEMBER INSERTABLE INSIDE A BONE STRUCTURE OF A HUMAN OR ANIMAL BODY, AND RELATED LOCATING SYSTEM This application is a §371 National Stage Application of International Application No. PCT/IB2005/001355, filed on 6 May 2005, claiming the priority of Italian Patent Application No. TO2004A000292 filed on 6 May 2004.

TECHNICAL FIELD

The present invention relates to a connecting member insertable inside a bone structure of a human or animal body, and to a locating system for determining at least one predetermined reference point in the connecting member.

More specifically, the present invention relates to a system for determining externally, and with no contact, the location of one or more reference points in a connecting member inserted inside a bone structure of a human or animal body; to which application, the following description refers purely by way of example.

BACKGROUND ART

As is known, in the treatment of bone fractures and/or breaks, particularly of "long" bones, such as the femur, tibia or humerus, one or more connecting members, typically comprising metal pins, are inserted inside the medullary canal of the bone to immobilize the bone fracture and prevent any relative rotation between the fractured bone portions.

Systems of the above type substantially comprise inserting a metal pin inside the medullary canal of the bone through an incision in the skin; and subsequently anchoring the pin to the bone portions by means of screws—so-called proximal and distal screws—each of which is connected and fixed to the metal pin at a respective reference point or so-called "gauge point".

The reference point is typically located at a transverse through hole formed in the body of the metal pin to receive the stem of a respective screw and anchor the pin to the bone portions. More specifically, the reference points of proximal screw holes are located on an end portion of the metal pin located, in use, at the skin incision, while the reference points of distal screw holes are located on the opposite end portion of the metal pin located, in use, further away from the skin incision.

When anchoring the pin, the reference points of the proximal screws are fairly easy to determine from the outside, whereas determining the reference points of the distal screw holes is extremely complicated.

Once the metal pin is inserted inside the medullary canal, the reference points are currently determined with the aid of a radioscopic system comprising an external device for emitting a diverging beam of X-rays onto the limb into which the pin has been inserted, and an X-ray detector for determining the X-ray absorption pattern in the area traversed by the beam, and displaying a radiological image of the limb and associated pin on a screen. In actual use, the surgeon determines a reference point on the basis of the radioscopic image, which also shows, instant by instant, the position of the drill bit before and as the bone portion is drilled from the outside.

The above radioscopic system has the major drawback of not allowing the surgeon to determine the reference points quickly and accurately. That is, the radioscopic image shows the surgeon the location of the reference point in a two-dimensional plane, but gives no indication of its location in the third dimension. As a result, the surgeon is forced to determine the reference point by highly invasive trial and error, during which, both the surgeon and patient are exposed to X-rays, with obvious harmful effects on the health of the patient, and particularly of the surgeon who is exposed repeatedly to such radiation.

EP-A-1.195.143 discloses a connecting member able to be inserted inside a bone structure. The connecting member comprises at least one electrical signal generator located at a predetermined reference point of the connecting member.

U.S. Pat. No. 6,080,099 discloses a seed including a capsule containing a radioisotope for radio-therapeutic use.

DISCLOSURE OF INVENTION

It is an object of the present invention to provide a locating system for determining a reference point in a connecting member inserted inside a bone structure of a human or animal body, designed to eliminate the aforementioned drawbacks.

According to the present invention, there is provided a connecting member insertable inside a bone structure of a human or animal body, as claimed in claim 1.

According to the present invention, there is also provided a locating system for determining at least one reference point in the connecting member, as claimed in claim 13.

According to the present invention, there is also provided a capsule, as claimed in claim 16.

BRIEF DESCRIPTION OF THE DRAWINGS

A non-limiting embodiment of the present invention will be described by way of example with reference to the accompanying drawings, in which.

BEST MODE FOR CARRYING OUT THE INVENTION

Figure 1:
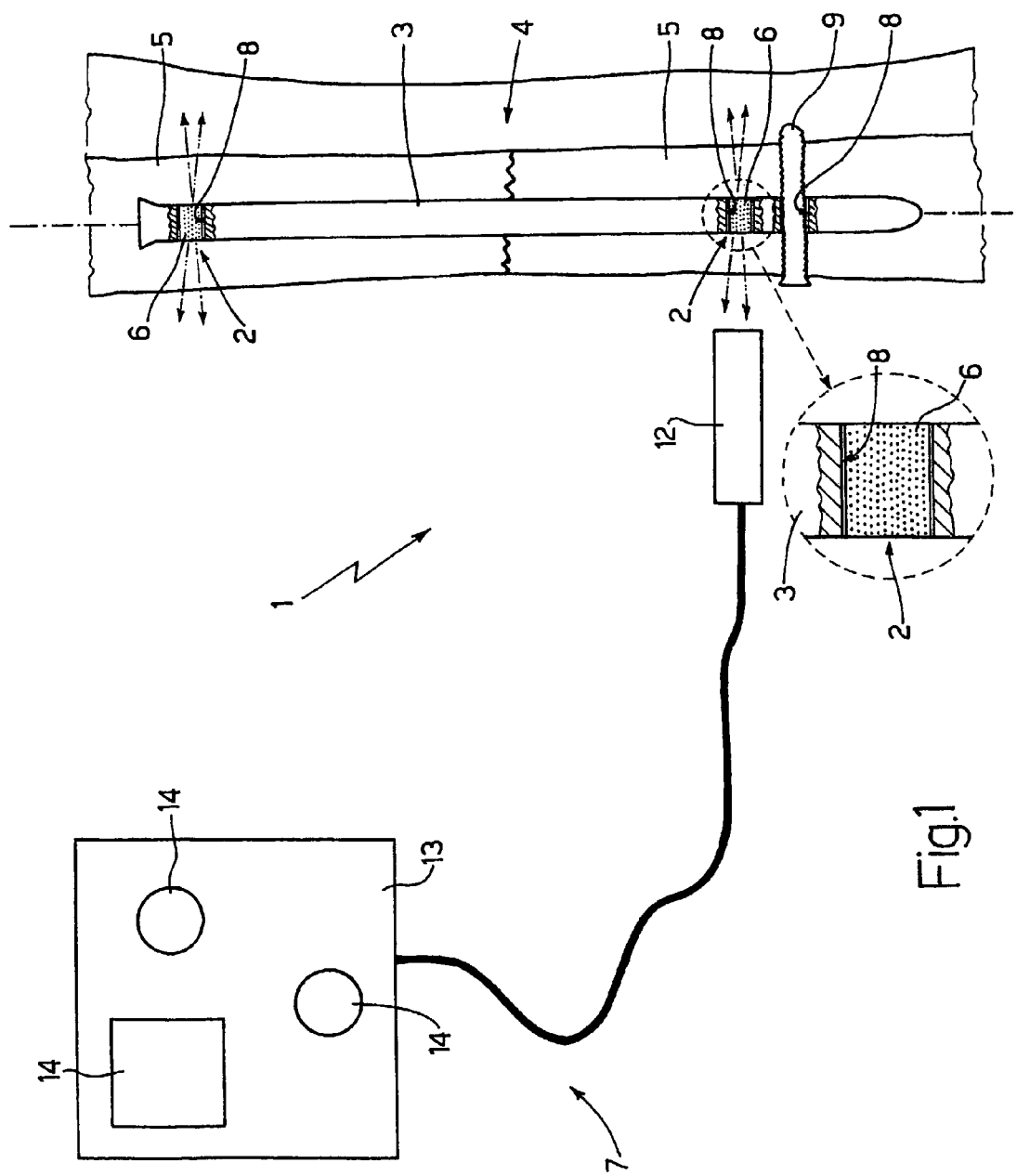
FIG. 1 shows, schematically, a locating system, in accordance with the present invention, for determining a predetermined reference point in a connecting member insertable inside a bone structure of a human or animal body.

Number 1 in FIG. 1 indicates as a whole a system for determining, externally and with no direct contact, the location of one or more reference points 2 in a connecting member 3 inserted, at a fracture, inside a bone structure 4 of a human or animal body to secure at least two fractured bone portions 5.

System 1 substantially comprises at least one dot radioactive source 6 insertable inside connecting member 3, at a respective reference point 2, to emit a beam of ionizing radiation outwards of bone structure 4 and, therefore, of the human or animal body; and an ionizing radiation detector 7 for measuring the ionizing radiation generated by dot radioactive source 6, and accordingly indicating the location of radioactive source 6 inside connecting member 3.

In other words, in actual use, detector 7 measures the ionizing radiation to indicate the location of each radioactive source 6 in connecting member 3, and so locate the corresponding reference point 2 in connecting member 3.

In the FIG. 1 example, connecting member 3 is defined by a rod or pin 3 preferably, though not necessarily, made of metal or any similar rigid material, and is insertable appropriately inside bone structure 4 to connect, i.e. join, fractured bone portions 5.

More specifically, at each reference point 2, pin 3 comprises a seat for housing radioactive source 6 and defined by a through hole 8, which extends substantially crosswise to the longitudinal axis of pin 3 and, in use, houses an anchoring device 9 for fixing pin 3 rigidly to bone portions 5.

In the FIG. 1 example, each anchoring device 9 is defined by a pin or a preferably metal screw, which is inserted appropriately inside a respective hole 8 and partly inside bone structure 4 to connect bone structure 4 and pin 3 rigidly and prevent any relative rotation between bone portions 5.

Radioactive source 6 is located inside pin 3, at a respective reference point 2, to outwardly emit a beam of ionizing radiation with a frequency preferably, though not necessarily, within the gamma radiation frequency spectrum. In the example shown, radioactive source 6 may be a gamma-emitting or beta-gamma-emitting radiation source.

More specifically, in the FIG. 1, 2, 3, 4 example, radioactive source 6 is defined by a capsule 10 comprising an outer shell 11, and a predetermined amount of gamma-emitting or beta-gamma-emitting radioactive material housed inside shell 11.

More specifically, shell 11 is shaped so as to be insertable inside any hole 8 in connecting member 3 and to emit ionizing radiation at reference point 2, which can thus be located from the outside to permit location of relative through hole 8.

Figure 2:
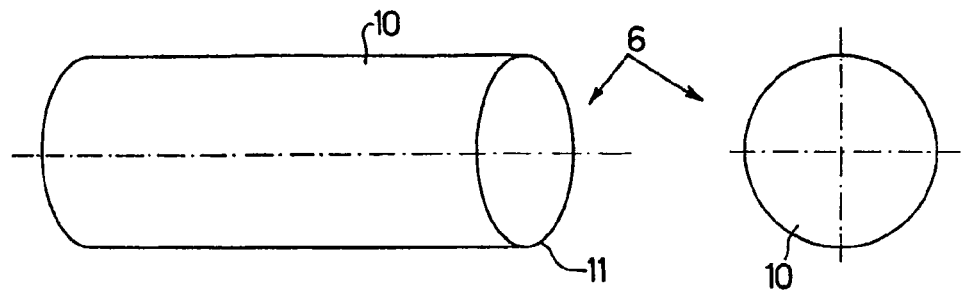
FIGS. 2 to 4 show, schematically, different embodiments of a radioactive source employed in the FIG. 1 locating system.

In the FIG. 2 example, each shell 11 is substantially cylindrical and sized to fit appropriately inside hole 8 in pin 3, and the radioactive material preferably comprises a gamma-emitting or beta-gamma-emitting radioisotope. In the example shown, the radioisotope may, for example, be technetium 99 m (Tc99m), iodine-123 (I123), indium-111 (In111), cobalt (Co57) or any other similar gamma-emitting or beta-gamma-emitting radioisotope with a predetermined decay time (half-life).

Figure 3:
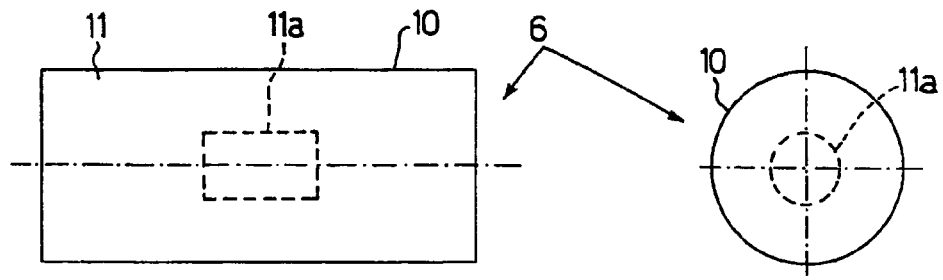
Figure 4:
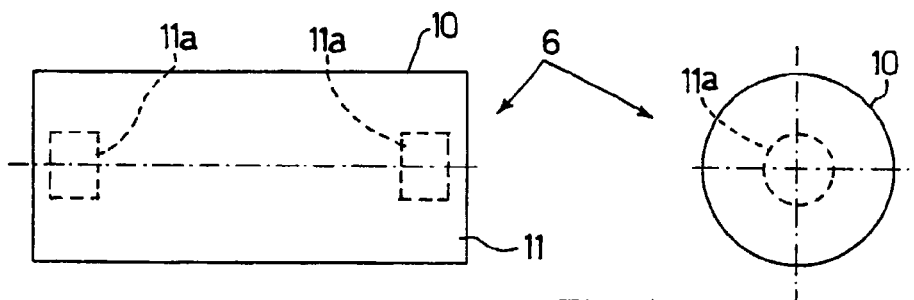

With reference to FIGS. 2, 3, 4, shell 11 is preferably, though not necessarily, made of biocompatible, reabsorbable, or any other similar type of material, and has an inner cavity 11a of predetermined volume for housing a quantity of gamma-emitting or beta-gamma-emitting material ranging between 3.7 and 37 MBq (0.01-1 mCi).

In the FIG. 4 variation, shell 11 of capsule 10 comprises two inner cavities 11a containing respective predetermined quantities of gamma-emitting or beta-gamma-emitting material, which are located at the two axial ends of shell 11 to emit a beam of ionizing radiation outwards from each end and so indicate, in use, the location of the two axial ends of shell 11. In addition to reference point 2, it is thus possible to advantageously also determine the inlet and outlet points of hole 8, so that anchoring screw 9 may be inserted perfectly coaxial with through hole 8.

In connection with the above, it should be pointed out that shell 11 may be of any external shape, and may be at least partly made of gamma-emitting or beta-gamma-emitting material.

Each capsule 10 may be housed inside hole 8 irremovably or so that it can be removed easily.

More specifically, if inserted irremovably, capsule 10 may be fixed to hole 8 by direct integration in the body of pin 3, or using adhesive, or by interference, or by means of any known type of mechanical click-on connecting system, so that it can be removed when drilling bone structure 4.

If inserted removably, capsule 10 may be fixed temporarily to hole 8, e.g. by means of an adhesive substance, so as not to escape accidentally from the hole when inserting pin 3 inside bone structure 4, but in such a manner that it can later be withdrawn before or when inserting anchoring pin or screw 9 inside through hole 8.

With reference to FIG. 1, detector 7 substantially comprises a measuring sensor 12 for indicating the intensity of the gamma or beta-gamma radiation striking the sensor; and a signal unit 13, which receives the gamma or beta-gamma radiation measurement from sensor 12, and generates an acoustic/visual signal when the ionizing radiation measurement satisfies a given relationship with a predetermined threshold.

In the FIG. 1 example, sensor 12 is a portable surgical probe, which can be moved by the surgeon along the patient's body as required to measure the ionizing radiation emitted by each radioactive source 6, and is connected to signal unit 13 to supply the surgeon with an instantaneous radiation measurement signal.

Signal unit 13 is defined by a processing device for receiving the measurement signal, comparing it with a predetermined radiation threshold, and generating an acoustic/visual signal by means of a number of acoustic/visual devices 14 when the ionizing radiation measurement is above or equal to the predetermined radiation threshold. In other words, signal unit 13 indicates acoustically/visually when probe 12 is positioned at the reference point 2 in pin 3.

In actual use, capsule 10 is inserted inside a corresponding hole 8 in pin 3 before pin 3 is inserted inside bone structure 4. Once pin 3 is inserted, the surgeon moves probe 12 over the patient's body, over the bone structure into which pin 3 has been inserted. When probe 12 is located at reference point 2, signal unit 13 picks up an ionizing radiation peak above the predetermined radiation threshold, and generates an acoustic/visual signal to inform the surgeon that the end of probe 12 is positioned correctly at reference point 2, thus determining externally the location of reference point 2.

System 1 has numerous advantages. In particular, it is extremely accurate, by indicating the exact location of reference point 2 in a three-dimensional space, thus enabling the surgeon to determine more accurately and less invasively the point in bone structure 4 in which to drill the hole in which to insert the anchoring screw of pin 3. As stated, precision is further enhanced in the case of connecting members 3 featuring capsules with two inner cavities 11a, which enable the inlet and outlet points of hole 8 to be determined externally, so that, when drilling the bone portion, the drill bit can be aligned correctly with the axis of hole 8. In this case, detector 7 may obviously be provided with two probes 12 for measuring the ionizing radiation emitted by each cavity 11a and so indicating the locations of the inlet and outlet points of the same hole 8.

System 1 also has the advantage of being extremely cheap and easy to produce, and of permitting extremely fast location of reference point 2, thus greatly reducing overall operating time, with obvious benefits to the patient and an obvious reduction in cost.

Finally, system 1 also has the advantage of drastically reducing exposure of both surgeon and patient to ionizing radiation. The radioactive source, in fact, contains such a small amount of radioactive material that, from the safety standpoint, patient and surgeon exposure to the ionizing radiation produced is therefore negligible.

Clearly, changes may be made to the system as described and illustrated herein without, however, departing from the scope of the present invention.

Figure 5:
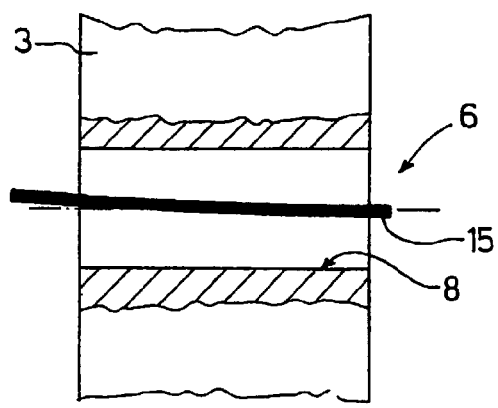
FIG. 5 shows a variation of the radioactive source employed in the FIG. 1 locating system.

More specifically, in the FIG. 5 variation, radioactive source 6 is defined by a thread 15 made at least partly of gamma-emitting or beta-gamma-emitting material and insertable inside through hole 8. The thread may, for example, be a suture of reabsorbable material impregnated with radioactive material.

In a further variation, not shown, radioactive source 6 is defined by an adhesive material at least partly made of gamma-emitting or beta-gamma-emitting material, and which is applied to hole 8.

Finally, in connection with the above, it should be pointed out that, as opposed to being located inside hole 8, reference point 2, and therefore relative radioactive source 6, may be located at any other reference point whose location must be determined externally. For example, radioactive source 6 may be located at one end of pin 3 to enable external location of the end when or after inserting pin 3 inside bone structure 4.

The invention claimed is:

1. A connecting member insertable inside a bone structure of a human or animal body, comprising:
   at least one dot radioactive source housed in a seat defined by a through hole extending substantially crosswise to a longitudinal axis of the connecting member and located at a predetermined reference point of the connecting member to emit a beam of ionizing radiation, which originates at said dot radioactive source, outwards of bone structure.

2. A connecting member as claimed in claim 1, wherein, said through hole, in use, receiving an anchoring screw for fixing said connecting member to said bone structure of the human or animal body.

3. A connecting member as claimed in claim 1, wherein said radioactive source emits gamma or beta-gamma ionizing radiation.

4. A connecting member as claimed in claim 1, wherein said radioactive source comprises a capsule made at least partly of radioactive material.

5. A connecting member as claimed in claim 4, wherein said radioactive material is a gamma-emitting or beta-gamma-emitting material.

6. A connecting member as claimed in claim 4, wherein said radioactive material is technetium 99 m (Tc99m) or iodine-123 (1123) or indium-111 (In111) or cobalt 57 (Co57).

7. A connecting member as claimed in claim 1, wherein said radioactive source comprises a capsule having a shell made of a material selected from the group consisting of a material biocompatible with said human or animal body, a material reabsorbable by said human or animal body, and combinations thereof.

8. A connecting member as claimed in claim 7, wherein said shell comprises at least one inner cavity containing said radioactive material.

9. A connecting member as claimed in claim 1, wherein said radioactive source comprises an adhesive substance at least partly made of radioactive material, and which is applied to the body of said connecting member at said predetermined reference point.

10. A connecting member as claimed in claim 1, wherein said radioactive source comprises at least one thread at least partly made of radioactive material.

11. A connecting member as claimed in claim 1, comprising a pin made of metal.

12. A locating system for locating at least one predetermined reference point in a connecting member insertable inside a bone structure of a reference point in a connecting member insertable inside a bone structure of a human or animal body, comprising
   a connecting member as claimed in claim 1; and
   a detector comprising measuring means which are positioned at said connecting member to measure the beam of ionizing radiation emitted by said dot radioactive source outwards of bone structure, and indicating means for indicating the position of said dot radioactive source in said connecting member as a function of the measured said radiation.

13. A connecting member as claimed in claim 12, wherein said measuring means comprise at least one probe which is positioned at said connecting member to detect ionizing radiation emitted by said radioactive source.

14. A connecting member as claimed in claim 13, wherein said indicating means comprise signaling means for generating a signal selected from the group consisting of an acoustical signal, a visual signal, and combinations thereof, when said ionizing radiation detected by said probe satisfies a given relationship with a predetermined reference threshold.

15. A capsule insertable inside a seat of a connecting member insertable inside a bone structure of a human or animal body, said capsule comprising:
   an outer shell substantially cylindrical and sized to fit inside said seat; and
   a dot radioactive source for emitting a beam of ionizing radiation outwards of bone structure to permit the location of said seat,
   said shell being made of a material selected from the group consisting of a material biocompatible with said human or animal body, a material reabsorbable by said human or animal body, and combinations thereof,
   wherein said shell comprises at least one inner cavity housing said dot radioactive source, and
   wherein said radiation originates at said dot radioactive source.

16. A connecting member as claimed in claim 15, wherein said shell comprises two inner cavities located at the two axial ends of the shell.

17. A connecting member as claimed in claim 16, wherein said radioactive material is gamma-emitting or beta-gamma-emitting material.

18. A connecting member as claimed in claim 16, wherein said radioactive material is technetium 99 m (Tc99m) or iodine-123 (1123) or indium-111 (In111) or cobalt (Co57).

19. A connecting member as claimed in claim 16, wherein said inner cavity or cavities are sized to house a quantity of radioactive material ranging between 3.7 and 37 MBq (0.01-1 mCi).

20. A connecting member as claimed in claim 15, wherein said radioactive material is a gamma-emitting or beta-emitting material.

21. A connecting member as claimed in claim 15, wherein said radioactive material is technetium 99 m (Tc99m) iodine-123 (1123) or indium-111 (In111) or cobalt (Co57).

22. A connecting member as claimed in claim 15, wherein said inner cavity or cavities are sized to house a quantity of radioactive material ranging between 3.7 and 37 MBq (0.01-1 mCi).

* * * * *

UNITED STATES PATENT AND TRADEMARK OFFICE
CERTIFICATE OF CORRECTION

PATENT NO. : 8,702,708 B2  
APPLICATION NO. : 11/568568  
DATED : April 22, 2014  
INVENTOR(S) : Ezio Visentin Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1717 days.

Signed and Sealed this

Twenty-ninth Day of September, 2015

Michelle K. Lee
*Director of the United States Patent and Trademark Office*